United States Patent
Williams et al.

[19]

[11] Patent Number: 5,847,759
[45] Date of Patent: Dec. 8, 1998

[54] COMBINATION ELECTRONIC IRIS AND CONNECTOR FOR USE WITH A LIGHT SOURCE

[76] Inventors: Ronald R. Williams, 24872 Sea Aire, Dana Point, Calif. 92629; Leonard Scrivo, 12 Crawford Dr., Tuckahoe, N.Y. 10707

[21] Appl. No.: 778,827

[22] Filed: Jan. 3, 1997

[51] Int. Cl.$^6$ .................................................. H04N 5/238
[52] U.S. Cl. .......................... 348/363; 348/66; 348/374; 600/132
[58] Field of Search ................................ 348/42, 45, 65, 348/66, 363, 359, 296, 249, 228, 229, 68, 72, 75, 76, 376, 374, 85; 600/101, 109, 178, 180, 132; 433/29, 31

[56] References Cited

U.S. PATENT DOCUMENTS

| | | | |
|---|---|---|---|
| 3,918,814 | 11/1975 | Weiser | 356/375 |
| 4,704,660 | 11/1987 | Robbins | 362/32 |
| 4,754,328 | 6/1988 | Barath et al. | 348/67 |
| 5,049,070 | 9/1991 | Ademovic | 348/66 |
| 5,289,555 | 2/1994 | Sanso | 385/92 |
| 5,309,330 | 5/1994 | Pillers et al. | 362/32 |
| 5,523,782 | 6/1996 | Williams | 348/66 |
| 5,528,432 | 6/1996 | Donahoo | 348/66 |
| 5,669,769 | 9/1997 | Disel | 433/29 |
| 5,737,013 | 4/1998 | Williams etal. | 348/66 |

*Primary Examiner*—Wendy Garber
*Assistant Examiner*—Aung S. Moe
*Attorney, Agent, or Firm*—W. Edward Johansen

[57] ABSTRACT

A combination electronic iris and connector for use with a light source, an optical fiber and a CCD, which is optically coupled to the optical fiber, includes a socket, a plug, a heat sink and an electronic iris. The socket has a threaded bore and is mechanically coupled to the light source. The plug is adapted to be coupled to the socket and has a bore for receiving the optical fiber. The heat sink has a disc-shaped portion having a bore for receiving the optical fiber and a threaded stem portion having a bore for receiving the optical fiber. The disc-shaped portion of the heat sink is slidably coupled to the light source and disposed adjacent to the socket. The threaded stem portion of the heat-sink is threadedly coupled in the threaded bore of the socket. The optical fiber is optically coupled to the light source. The electronic iris is disposed within the light source and axially aligned with the optical fiber. The electronic iris is controlled by feedback from the CCD from a feedback circuit.

2 Claims, 5 Drawing Sheets

COMBINATION ELECTRONIC IRIS AND CONNECTOR FOR USE WITH A LIGHT SOURCE

BACKGROUND OF THE INVENTION

The field of the invention relates to a combination electronic iris and connector for use with a light source.

U.S. Pat. No. 5,258,848 teaches an exposure control apparatus which includes a control amount converting table for storing data on a gain control amount associated with data on a detected quantity of incident light. On the basis of an output from the control amount converting table, light quantity gains of a light quantity variable mechanism, such as an iris, a shutter or an AGC amplifier, are set. The level of a quantity of incident light coming through these light quantity variable mechanisms is detected, and the detected data is fed to a correcting mechanism. The correcting mechanism corrects an error between data on the control amount of the light quantity gain output from the control amount converting table and an actual light quantity gain of the light quantity variable mechanism. An output from the correcting mechanism is fed to the control amount converting table.

U.S. Pat. No. 4,300,167 teaches an automatic iris control system which is electrically adjustable. The automatic iris control system is adapted to be connected between a video camera and an optical input device which produces an optical image from a light directed upon and reflected from a subject. The optical image is directed onto the surface of an electronic imaging tube in the video camera and the optical image has a wide variation of reflected light due to variations in distance of the subject from the light source. The automatic iris control system has an adjustable iris and a drive motor located between the surface of the electronic imaging tube. The optical input device dynamically varies the intensity of the optical image applied to the electronic imaging tube of the video camera. A light intensity programming circuit establishes a desired light intensity level on the surface of the electronic imaging tube of the video camera. An automatic iris control circuit has a low gain amplifier, a weighted peak response detector, a comparator and a circuit which controls current to the iris drive motor. Another circuit provides a feedback signal which represents the direction in which the iris must be adjusted by the motor to control the light intensity on the surface of the electronic imaging tube of the video camera.

U.S. Pat. No. 5,410,225 teaches in a video camera in strobe mode, when a condition for strobe light emission is ready, the aperture of an iris is reduced and the gain of an AGC amplifier is fixed at a predetermined value. Accordingly, a dark image representing the condition ready for strobe light emission is displayed on an electronic view finder. Additionally saturation of charge accumulation is prevented.

U.S. Pat. No. 5,422,669 teaches a solid state imaging apparatus which prevents occurrence of small aperture fading by diffraction of light and can control the amplitude level of an image signal within a prescribed range. The solid state imaging apparatus employs a solid state imaging element such as a CCD. When the level of an image signal outputted from the solid state imaging element exceeds a predetermined value, a driving motor is driven to effect adjustment of a mechanical iris. The capacitance of a variable capacitance diode provided in a voltage converting section of the solid state imaging element is controlled in accordance with the amplitude level of the image signal to control the voltage conversion efficiency of the voltage converting section of the solid state imaging element so as to fix the level of the image signal linearly in their entirety to the horizontal direction or may be of a chevron shape.

U.S. Pat. No. 4,431,288 teaches a camera with a liquid crystal aperture stop means which has a shift means adapted to shift the liquid crystal aperture stop means between a plurality of positions depending upon exposure conditions.

U.S. Pat. No. 5,047,847 teaches a liquid crystal assembly forming at least a part of an image optical system which consists of a plurality of liquid crystals having a refractive index anisotropy and having different response frequencies of molecule orientation so that the transmittivity and refractive index of the plurality of liquid crystals may be independently controlled with few signal lines by varying the frequency of the driving signal applied to the liquid crystal assembly.

U.S. Pat. No. 3,555,181 teaches an automatic video level control which employs iris and amplifier gain adjustments.

U.S. Pat. No. 4,155,619 teaches a connector which includes a plug and a socket. The connector is for use with a coaxial cable with armoring. The plug is a tubular body which includes a plug-in element, a bushing and a clamping element. The bushing is fastened to the tubular body in order to hold a coaxial cable. The clamping element is clamped on the bushing around the armoring of the coaxial cable. The tubular body is a single piece having without interruption of continuity two separate zones one of which constitutes the plug-in element and the other of which the clamping element.

In the prior art an illumination system includes a lamp assembly with a light bulb, a concave reflector, a fan and a bundle of optical fibers. The concave reflector condenses light energy and reflects it into the bundle of optical fibers. The fan dissipates the heat which the light bulb generates. Due to the large size of the illumination system, it is usually located relatively far away from the work area. The remote positioning of the illumination system necessitates the use of a relatively long bundle of optical fibers. Due to the light losses inherent in the bundle of optical fibers, which losses can be as high as fifty percent per meter, the light bulb used must emit light of a high intensity and therefore, it must have a relatively high wattage. One disadvantage of using high wattage bulbs is that they have a relatively short operating life. Another disadvantage is that the high emission of heat will inconvenience the operator as well as the patient. Furthermore, a relatively large fan must be used to cool the illumination system whereby the size of the fan creates an undesired increase in the overall size of the illumination system and produces disturbing noise.

For many years, fiber optic illumination systems have used bundles of optical fibers to transmit light to dental and medical instruments. One end of each bundle of optical fibers is conventionally inserted into an opening in a socket which is aligned with a light source. The light from the light source is transmitted through the bundle of optical fibers to the dental or medical instrument at the other end of the bundle of optical fibers.

European Patent Application filed Oct. 18, 1982 under Ser. No. PCT/SE82/00337 discloses an illumination system which is relatively compact and which includes a lens and reflector. The lens and the reflector are combined to form a condensing system which is designed to concentrate light emitted from a relatively low wattage light bulb on a light-receiving end of a bundle of optical fibers. Because its light is concentrated, the low wattage bulb can illuminate the light-receiving end of the bundle of optical fiber to the same extent as a higher wattage light bulb. The use of the low wattage light bulb is advantageous in that it takes up less room and generates less heat than a high wattage light bulb. However, in order to illuminate more than one bundle of optical fibers and therefore more than one instrument, the lens of the condensing system is adapted so as to be switchable between two or more bundles of optical fibers. Each bundle of optical fibers may be selectively and independently coupled to the light bulb. Although the switch permits a plurality of bundles of optical fibers to be illuminated, they can not be illuminated simultaneously. The provision of such a light switch is also disadvantageous in that it requires a manual switching operation.

U.S. Pat. No. 3,758,951 teaches an illumination system which includes a control module for controlling the intensity of the light source. The control module is adapted to be mounted on a dental tray. The use of the control module which is separate from the light source provides a convenient mechanism for controlling the intensity of the light source and one which utilizes a minimum portion of a dentist's working area. A dental handpiece hose receives a bundle of optical fibers which is connected to the light source. The dental handpiece hose includes the usual conduits and a further conduit disposed between conduits for receiving the bundle of optical fibers. One of the walls defining the further conduit may be made up of a pair of elongated interlocking members which permit the wall to be partially or completely opened for ready access to the further conduit.

U.S. Pat. No. 4,579,419 teaches a connector which includes an optical fiber element having a light-receiving end with a transverse cross-sectional shape which complements the transverse cross-sectional shape of a light-receiving end of another optical fiber element. The complementarily shaped light-receiving ends permit a plurality of optical fiber connectors to be arranged alongside one another so that they may be directly and simultaneously illuminated by a single beam of light emitted from a source of light.

U.S. Pat. No. 4,896,939 teaches a cable which includes an optical fiber, a first tubular electrical conductor, a second tubular electrical conductor and a dielectric support. The first tubular electrical conductor encloses the optical fiber. The second tubular electrical conductor encloses the first tubular electrical conductor. The dielectric support element is disposed between the first and second tubular electrical conductors in order to maintain the first and second tubular electrical conductors in a coaxial relationship. A connector includes a plug and a socket and connects respective electrical and optical elements of the cable.

U.S. Pat. No. 3,638,013 describes an illumination system which includes a rotatable plug having three bundle-receiving openings. The plug may be rotated so that one, two or all three of the openings are positioned to be illuminated by a light source so that a corresponding number of instruments can be lit.

U.S. Pat. No. 4,208,579 teaches an apparatus for use in operating a dental drill in which the air, water and light for the hand-held drill member are each delivered from an associated supply source, all of which are adapted to be located at a position remote from the working end of the drill and are coupled to the drill through a conduit cable. A control mechanism for the selective energization of the light supply source is located within easy reach of the operator to permit turn-on and/or turn-off of the light supply source through a simple fingertip control which is provided within a remote control unit which is totally electrically isolated from the high voltage present in the light supply source in order to protect both the operator and the patient from either shock or injury. The light supply source may be automatically energized merely by lifting the dental instrument containing a bundle of optical fiber. The apparatus may be independent of the dental drill in order to permit a wide variety of uses independently of its use with the dental drill.

U.S. Pat. No. 3,897,134 and U. S. Pat. No. 4,014,098 teach an optical fiber element which includes a first bundle of optical fibers, a support member and a yieldable member. The first bundle of optical fibers has at least two optical faces. The support member supports at least a portion of the bundle of optical fibers with one optical face in a desired initial position. The yieldable member cooperates with the first bundle of optical fibers in order to permit movement of one optical face relative to its initial position upon application of pressure to one optical face. The optical fiber element is especially adapted for use in combination with a dental handpiece in a manner such that one optical face extends through the turbine housing portion of the dental handpiece. The optical fiber element also includes a tubular guide member, a resilient support member in the form of a flexible tubular member and a plunger assembly. The first bundle of optical fibers extends through each of the above components. The other optical face of the optical fiber element is adapted to be coupled under compression and in face to face alignment with a light emitting face of a second bundle of optical fibers, which is connectable to a light source, to complete a light path to the light source.

The inventors incorporate the teachings of U. S. Pat. No. Des. 245,977, U.S. Pat. No. 3,360,763, U. S. Pat. No. 3,885,851, U.S. Pat. No. 2,958,845, U. S. Pat. No. 3,089, 115, U.S. Pat. No. 3,160,457, U. S. Pat. No. 3,195,905 and the above-cited patents into this specification.

SUMMARY OF INVENTION

The present invention is generally directed to a combination electronic iris and connector for use with a light source, an optical fiber and a CCD which is optically coupled to the optical fiber.

In a first, separate aspect of the present invention, the combination electronic iris and optical connector includes a socket, a plug, a heat sink and an electronic iris. The socket has a threaded bore and is mechanically coupled to the light source. The plug is adapted to be coupled to the socket and has a bore for receiving the optical fiber. The heat sink has a disc-shaped portion having a bore for receiving the optical fiber and a threaded stem portion having a bore for receiving the optical fiber. The disc-shaped portion of the heat sink is slidably coupled to the light source and disposed adjacent to the socket. The threaded stem portion of the heat-sink is threadedly coupled in the threaded bore of the socket. The optical fiber is optically coupled to the light source. The electronic iris is disposed within the light source and axially aligned with the optical fiber. The electronic iris is controlled by feedback from the CCD from a feedback circuit.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE PREFERRED EMBODIMENTS

Figure 1:
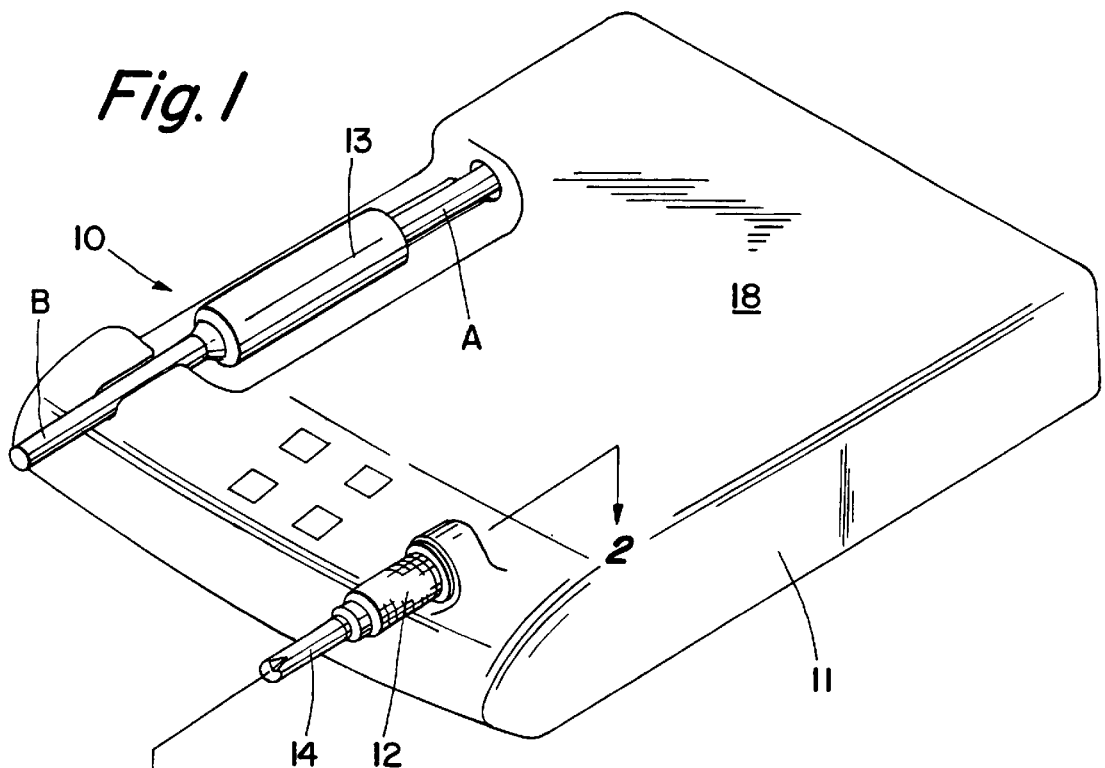
FIG. 1 is a perspective drawing of a dental video camera, a cable which has an optical fiber and a plurality of electrical wires and a combination light source and connector which includes a light source having a housing with a front, a side and a top, and a quick connect/ disconnect connector having a plug according to the invention.

Referring to FIG. 1 a combination light source and connector 10 which includes a light source 11 and a quick connect/disconnect connector 12, a dental video camera 13 and a cable 14. The cable 14 couples the dental video camera 13 to the light source 11 through the connector 12. The application which was filed under Ser. No. 08/560,397 teaches a dental video camera which includes a housing CCD camera, an adjustably focusing lens, a fixed focusing lens system. The CCD camera is disposed within the proximal portion of the housing. The adjustably focusing lens includes a first sleeve and a second sleeve. The first sleeve has a longitudinal axis. The first sleeve is axially aligned along the longitudinal axis and is disposed within the elongated cavity of the housing adjacent to the fixed focusing lens system. The first sleeve is able to rotate about the longitudinal axis and is restrained from moving laterally back and forth along the longitudinal axis. The second sleeve is telescopically and slidably coupled to the first sleeve. The second sleeve is able to move laterally back and forth along the longitudinal axis and is restrained from rotating about the longitudinal axis. A knob bi-directionally drives the second sleeve laterally to produce back and forth lateral movements along the longitudinal axis, however a slide mechanism may bi-directionally drives the second sleeve laterally to produce back and forth lateral movements along the longitudinal axis. The back and forth lateral movements of the second sleeve generates clockwise and counter-clockwise rotations, respectively, of the first sleeve. The adjustably focusing lens also includes a first achromatic lens, which is disposed in a first lens carrier, and a second achromatic lens, which is disposed in a second lens carrier. The first lens carrier with the first achromatic lens is disposed within and coupled to the first sleeve. The second lens carrier with the second achromatic lens is disposed within the first sleeve and is fixedly coupled to the first sleeve. The back and forth lateral movements of the second sleeve changes the position of the first and second achromatic lenses with respect to the position of the CCD camera thereby changing the field of focus. The adjustably focusing lens provides a focusing adjustment between a near field of focus and a far field of focus. The dental video camera also includes an electrically adjustable iris which is optically and mechanically coupled to the adjustably focusing lens system. The electrically adjustable iris is adjusted between a nearly closed opening and a wide open opening in response to the focusing adjustment between the near field of focus and the far field of focus. When the knob is in the neutral position the opening of the electrically adjustable iris is between nearly closed and wide open. When the knob has been rotated counter-clockwise forty five degrees from the neutral position the opening of the electrically adjustable iris is wide open.

U.S. Pat. No. 4,300,167 teaches an electrically adjustable iris which is a liquid crystal assembly forming at least a part of an image optical system. The liquid crystal assembly consists of a plurality of liquid crystals having a refractive index anisotropy and having different response frequencies of molecule orientation so that the transmittivity and refractive index of the plurality of liquid crystals may be independently controlled with few signal lines by varying the frequency of the driving signal applied to the liquid crystal assembly. U. S. Pat. No. 4,431,288 teaches an electrically adjustable iris.

Figure 2:
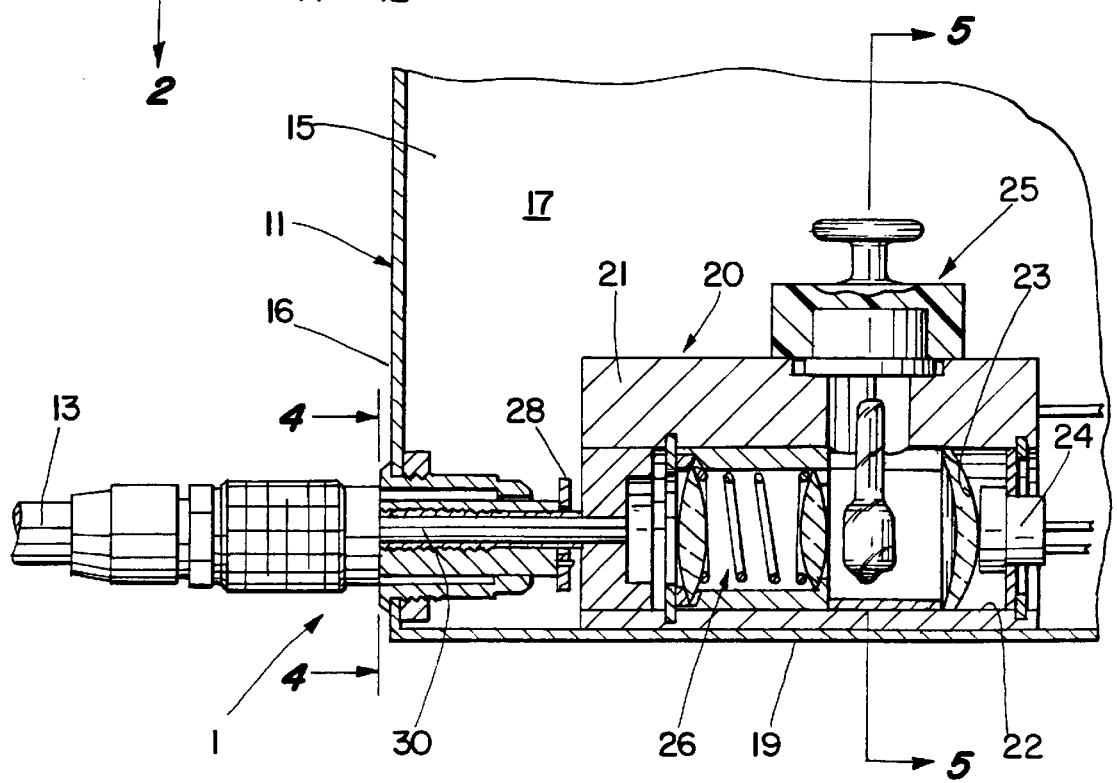
FIG. 2 is a front elevational view in partial cross-section of the front of the housing of the light source of FIG. 1 taken along the line 2—2 of FIG. 1.

Referring to FIG. 1 in conjunction with FIG. 2 the light source 11 includes a housing 15 with a front 16, a side 17, a top 18 and a bottom 19 and a light-tube module 20 which includes a body 21 with a cavity 22, a reflector 23, a heat sensor 24, a lamp assembly 25 and a focusing lens system 26. The reflector 23, the heat sensor 24, the lamp assembly 25 and the focusing lens system 26 are disposed within the cavity and are optically aligned with each other.

Figure 3:
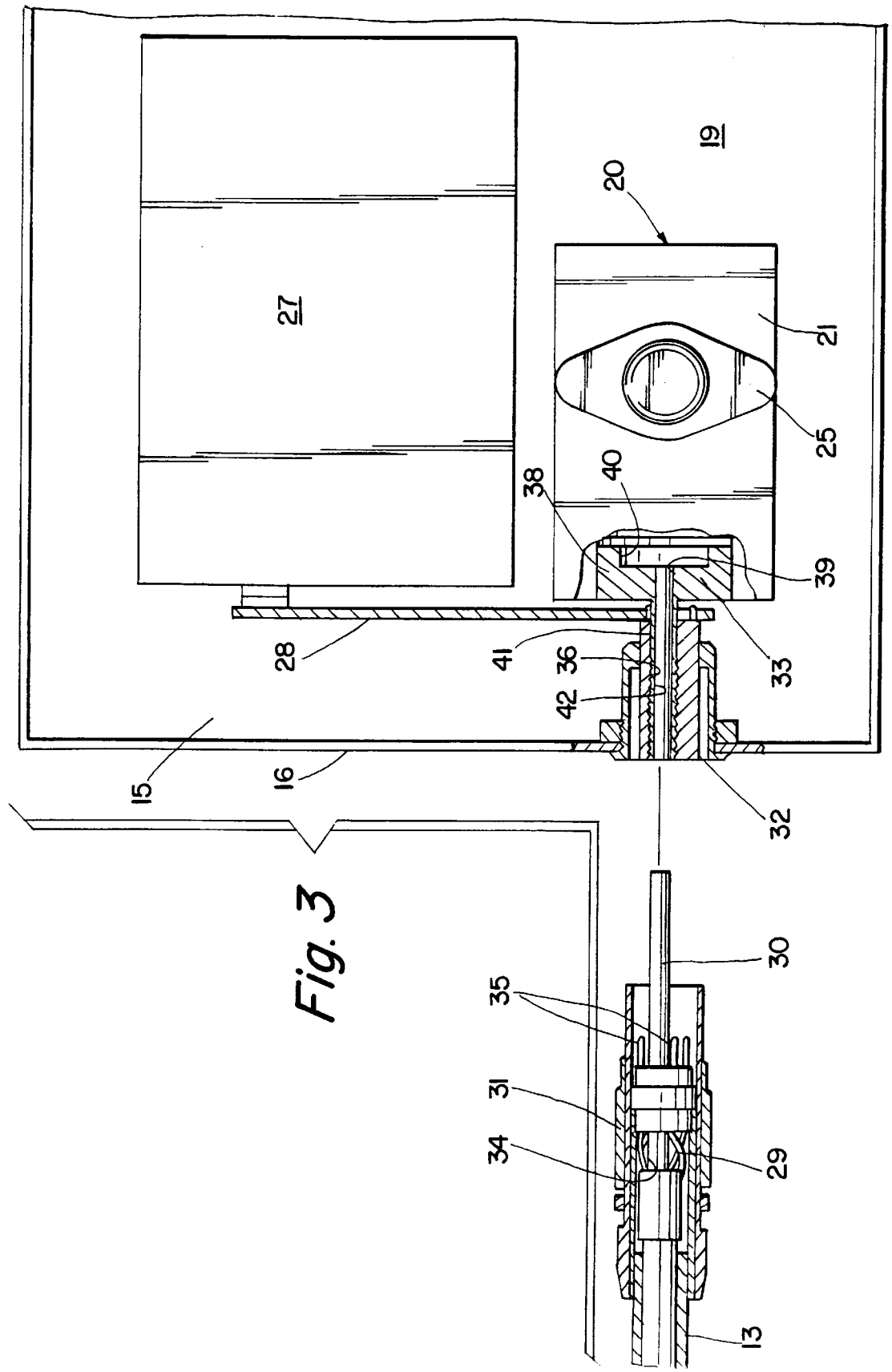
FIG. 3 is a partial, exploded, top plan view in partial cross-section of the combination light source and connector of FIG. 1 with the housing also having a bottom, a light-tube module, a circuit board and a processor being disposed on the bottom of the housing and the quick connect/ disconnect connector also having a socket and a heat sink.

Referring to FIG. 1 in conjunction with FIG. 3 the light source 11 also includes a processor 27 and a circuit board 28. The light-tube module 20 and the processor 27 are mechanically coupled to the bottom 19 of the housing 15. The circuit board 28 is electrically coupled to the processor 27.

Referring to FIG. 1 in conjunction with FIG. 3 the cable 13 has a plurality of electrical wires 29 and an optical fiber 30.

Referring to FIG. 2 in conjunction with FIG. 3 the quick connect/disconnect connector 12 has a plug 31, a socket 32 and a heat sink 33. The plug 31 has a bore 34 which receives the optical fiber 30. The plug 31 has a plurality of pins 35.

Figure 4:
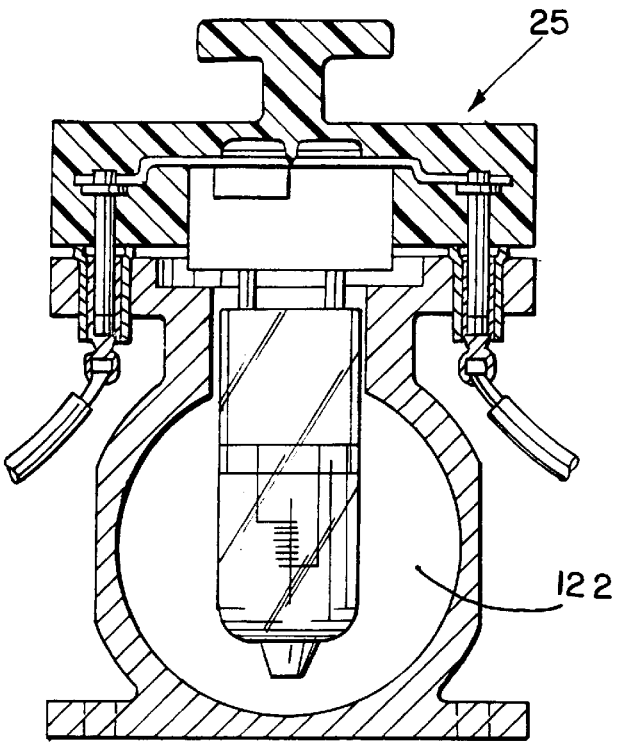
FIG. 4 is a transverse view in cross-section of the light-tube module of the combination light source and connector of FIG. 1 taken along the line 4—4 of FIG. 2.

Referring to FIG. 3 in conjunction with FIG. 4 the socket 32 has a threaded bore 36. The socket 32 is mechanically coupled to the front 16 of the housing 15. The plug 31 is adapted to be mechanically coupled to the socket 32 so that the bore 34 of the plug 31 is axially aligned with the threaded bore 36 of the socket 32. The socket 32 has a plurality of receptacles 37. Each pin 35 of the plug 31 is aligned with one of the receptacles 37 of the socket 32 in order to receive it.

Still referring to FIG. 3 in conjunction with FIG. 4 the heat sink 33 has a disc-shaped portion 38 with a first small bore 39 which receives the optical fiber 30 and a large bore 40 and a threaded stem portion 41 with a second small bore 42 which receives the optical fiber 30. The large bore 40 is axially alighted with the first small bore 39. The disc-shaped portion 38 of the heat sink 33 is slidably coupled within the cavity 22 of the body 21 of the light-tube module 20 and is disposed adjacent to the socket 32. The threaded stem portion 41 of the heat-sink 33 is threadedly coupled in the threaded bore 35 of the socket 32. The optical fiber 30 is slidably coupled into the bore 34 of the plug 31 and the first and second small bores 39 and 42 of the disc-shaped portion 38 and the threaded stem portion 40, respectively, of the heat sink 33. The stem portion 41 of the heat-sink 33 and the threaded bore 35 of the socket 32 do not have to be threaded. The quick connect/disconnect connector 12, the iris and cable 13 function together to dissipate heat which the light energy generates from the lamp assembly 25 produces.

Referring to FIG. 2 in conjunction with FIG. 3 the focusing lens system 26 includes a first lens 43, a sleeve 44, a second lens 45, a spring 47 and a first C-ring 48. The first lens 43 is slidably coupled within the sleeve 44. The second lens 45 is also slidably coupled within the sleeve 44. The cavity 22 of the body 21 of the light-tube 20 has a first ring groove 49, a second ring groove 50, a first cylindrical portion 51, a second cylindrical portion 52 and a third cylindrical portion 53. The diameters of the first and third cylindrical portions 51 and 53 is larger than the diameter of the second cylindrical portion 52 thereby forming a first retaining cylindrical edge 54 and a second retaining cylindrical edge 55. The focusing lens system 26 is formed by inserting serially at a first end 56 the sleeve 44 with the first lens 43, the spring 47 and the second lens 45 inserted therein. The first C-ring 48 is inserted and secured in the first ring groove 49. At a second end 57 the reflector 23, the heat sensor 24 and a washer 58 are inserted serially. A second C-ring 59 is inserted and secured in the second ring groove 50.

Referring to FIG. 2 in conjunction with FIG. 3 when the plug 31 is inserted in the socket 32 the optical fiber 30 is axially aligned with the focusing lens system 26 of the light-tube module 20. The optical fiber 30 extends to the end of the first small bore 39 of the disc-shaped portion 38 of the heat sink, but does not extend into the large bore 40 thereof. The circuit board 28 has a plurality of conductive lines 60 each of which is electrically coupled one of the receptacles 37 of the socket 32. A disc-shaped piece 61 of insulating material, such as a plastic material, maintains the electrical separation between the conductive lines 60 and the disc-shaped portion 38 of the heat sink 33. When the heat sensor 24 detects excessive heat on the reflector 23 and within the cavity 22 of the body 21, the heat sensor 24 sends a signal to the processor 27 which turns off the lamp assembly 25.

Figure 5:
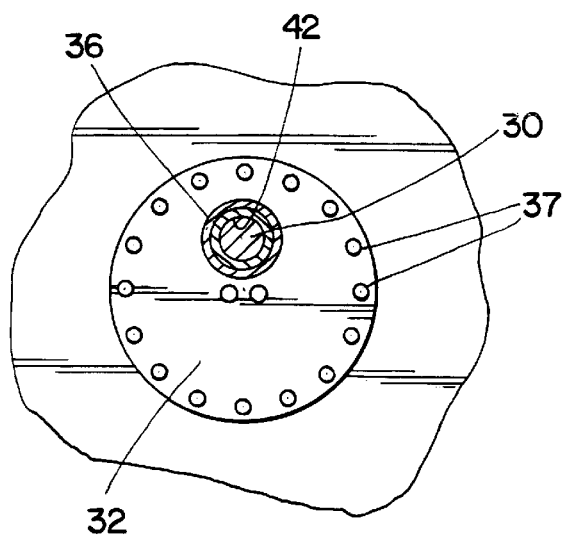
FIG. 5 is a longitudinal view in cross-section of a light-tube module of the light source of FIG. 1 which includes a body with a cavity, a temperature sensor, a reflector, a lamp assembly and a focusing lens system, also having a heat-sink and the optical fiber of the cable of FIG. 1 taken along the line 5—5 of FIG. 2.

Referring to FIG. 2 in conjunction with FIG. 5 the body 21 of the light-tube module 20 has a lamp bore 62, two top flanges 63 and an output bore 64. Each of the top flanges 63 has a socket bore 65. The lamp assembly 25 includes two hollow insulating sleeves 66, two hollow conducting sleeves 67 and two insulated conductive wires 68. Each of the two hollow insulating sleeves 66 is inserted in the socket bore 65 of one of the two top flanges 63. Each of the two hollow conducting sleeves 67 is inserted in one of the two insulating sleeves 66. Each of the two insulated conductive wire 68 is electrically coupled to one of the two hollow conducting sleeves 67. The lamp assembly 25 also includes a cap 69 which is formed out of an insulating material, such as plastic, and which has two pin bores 70, two conductive pins 71, two conductors 72 and a light bulb 73 with two terminals 74. The light bulb 73 is mechanically coupled to the cap 69 and is adapted to be inserted into the lamp bore 62. Each of the two conductive pins 71 is inserted in one of the two pin bores 70 of the cap 69 and is adapted to be inserted into one of the two conducting sleeves 67 so that each of the two conductive pins 71 can be electrically coupled to one of the two insulated conductive wires 68. Each of the two conductors 72 electrically couples one of the two conductive pins 71 to one of the two terminals 74 of the light bulb 73.

Figure 6:
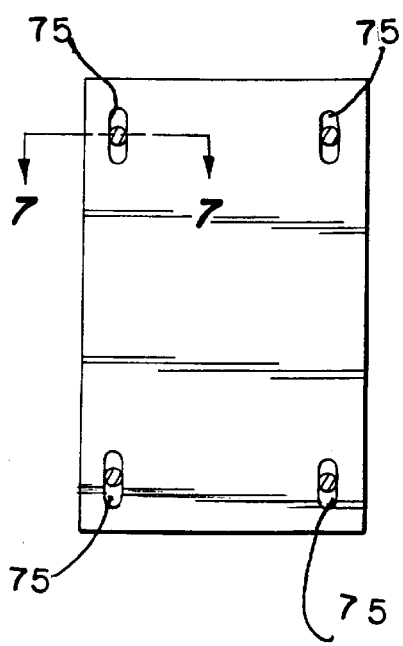
FIG. 6 is a partial, top plan view in cross-section of the housing of the light source of FIG. 1.
Figure 7:
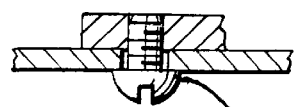
FIG. 7 is an enlarged partial, longitudinal view in cross-section of the housing of the light source of FIG. 1 taken along the line 7—7 of FIG. 6.

Referring to FIG. 2 in conjunction with FIG. 6 and FIG. 7 the bottom 19 of the housing 15 has four elongated slots 75. The body 21 of the light-tube module 20 has four threaded holes 76 which are arranged in the same manner as the four elongated slots 75. Each of four screws 77 is loosely inserted into one of the four elongated slots 75 and threaded coupled to one of the four threaded holes 76 in order to not only secure the light-tube module 20 in place, but also to provide focus adjustability of the light source 11 onto the optical fiber 30 by bi-directionally sliding the body 21 of the light-tube module 20 back and forth. The heat sink 33 is fixedly coupled to the socket 32, but is slidably coupled within the cavity of the body 21 of the light-tube module 20.

Figure 8:
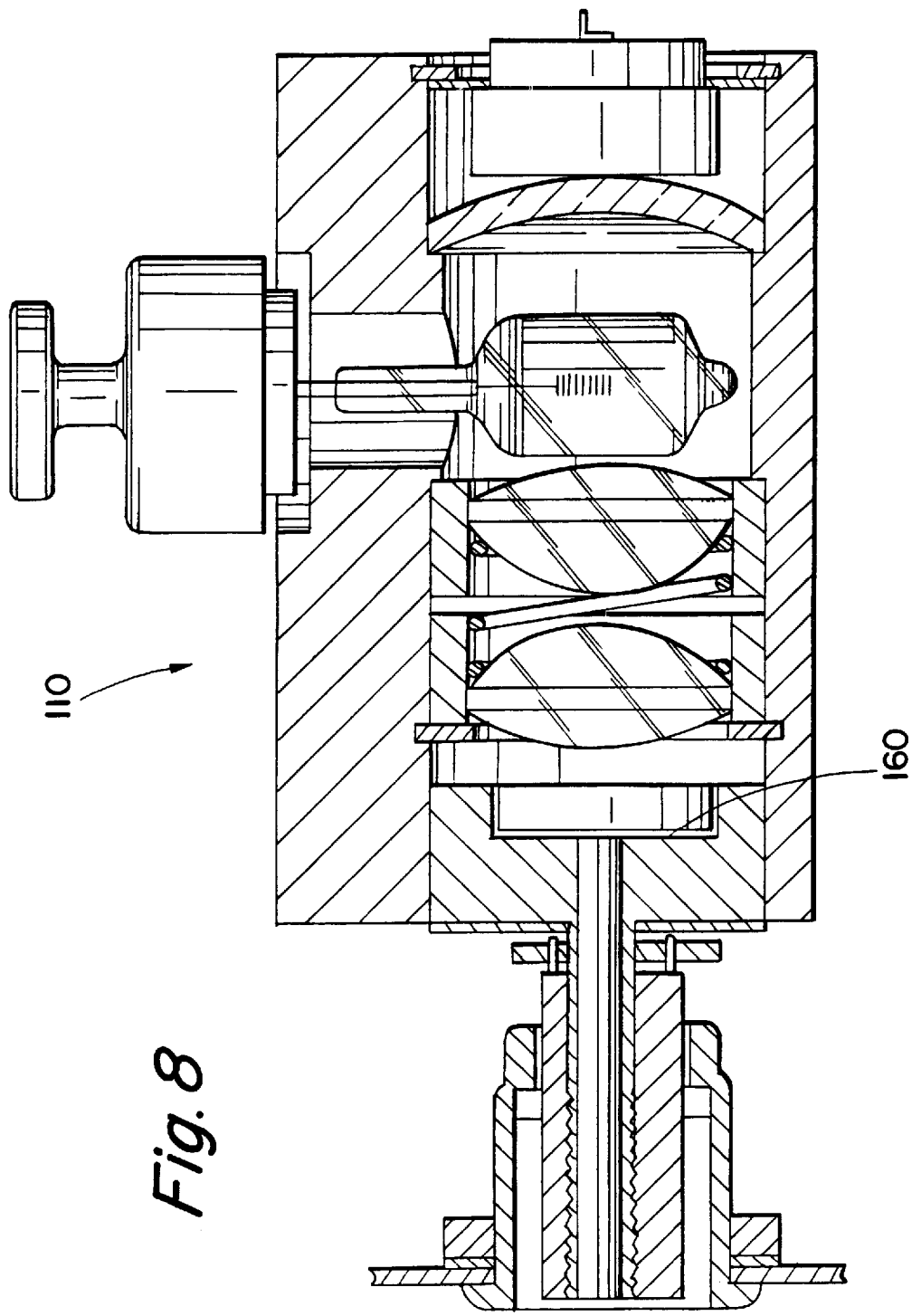
FIG. 8 is a front elevational view in partial cross-section of a light source of FIG. 1 according to the invention.

Referring to FIG. 8 a combination electronic iris and connector 110 is for use with a light source 111 and an optical fiber 112 and includes a connector 113. The light source 111 includes a light-tube module 120. The light-tube module 120 includes a body 121 with a cavity 122, a reflector 123, a heat sensor 124, a lamp assembly 125 and a focusing lens system 126. The connector 113 includes a plug 131, a socket 132 and a heat sink 133. A CCD is optically coupled to the optical fiber 112. The focusing lens system 126 includes a first lens 143, a first sleeve 144, a second lens 145, a second sleeve 146, a spring 147 and a first C-ring 148. The first lens 143 is slidably coupled within the first sleeve 144. The second lens 145 is slidably coupled within the second sleeve 146. The cavity 122 of the body 121 of the light-tube 120 has a first ring groove 149, a second ring groove 150, a first cylindrical portion 151, a second cylindrical portion 152 and a third cylindrical portion 153. The diameters of the first and third cylindrical portions 151 and 153 is larger than the diameter of the second cylindrical portion 152 thereby forming a first retaining cylindrical edge 154 and a second retaining cylindrical edge 155. The focusing lens system 126 is formed by inserting serially at a first end 156 the first sleeve 144 with the first lens 143 inserted therein, the spring 147 and the second sleeve 146 with the second lens 145 inserted therein. The first C-ring 148 is inserted and secured in the first ring groove 149. At a second end 157 the reflector 123, the heat sensor 124 and a washer 158 are inserted serially. A second C-ring 159 is inserted and secured in the second ring groove 150.

Figure 9:
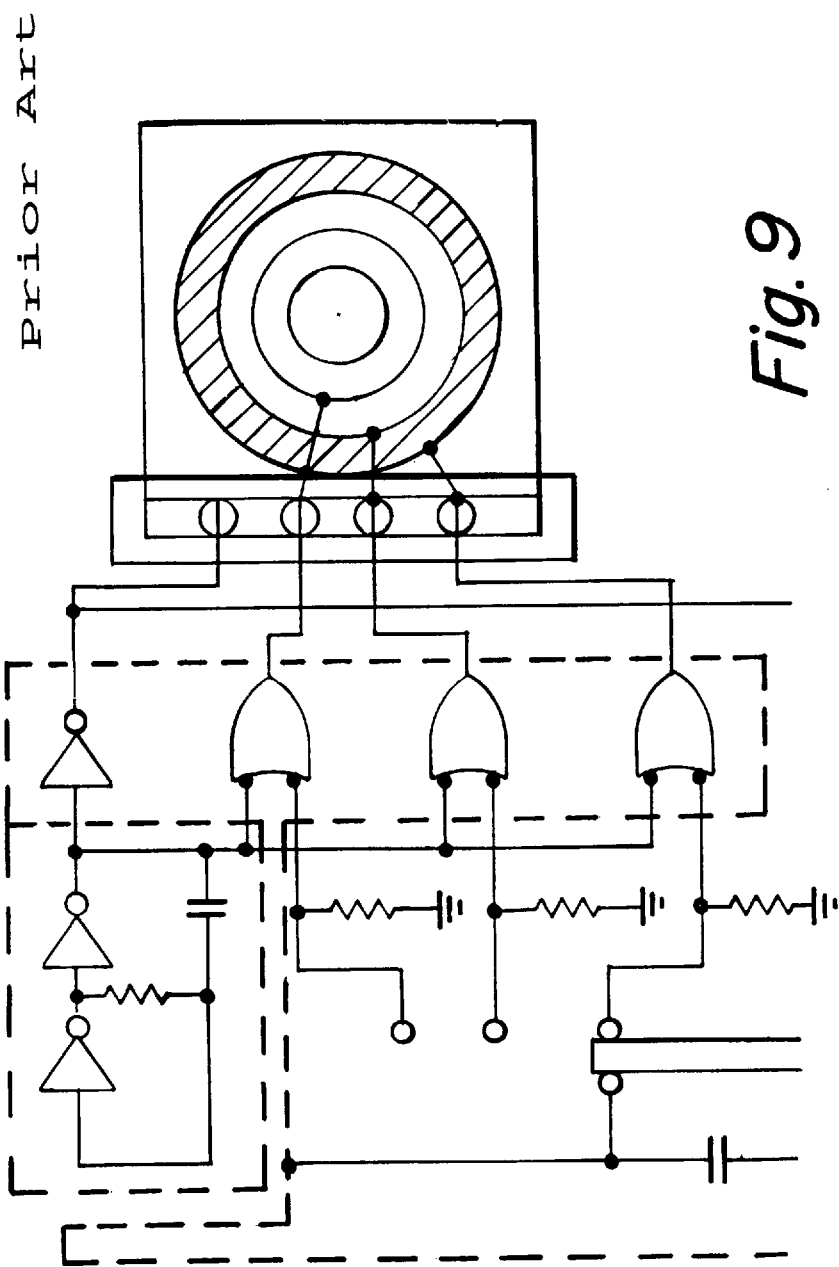
FIG. 9 is schematic drawing of an electronic iris.

Referring to FIG. 8 in conjunction with FIG. 3 and FIG. 9 the processor 28 includes an exposure control circuit which U. S. Pat. No. 5,258,848 teaches. The combination electronic iris and connector 110 also includes an electronic iris 160. The CCD includes a substrate with a plurality of charge coupled devices and detector. The substrate is optically coupled to the optical fiber. The detector is optically coupled to the charge coupled devices and electrically coupled to the electronic iris 160. The detector detects light intensity on the substrate and then either opens or closes the electronic iris 160 in a relative response thereto thereby controlling the light intensity on said substrate. The socket 132 has a threaded bore and is mechanically coupled to the light source 111. The plug 131 is adapted to be coupled to the socket 132 and has a bore for receiving the optical fiber 112. The heat sink 133 has a disc-shaped portion having a bore for receiving the optical fiber 112 and a threaded stem portion having a bore for receiving the optical fiber 112. The disc-shaped portion of the heat sink 133 is slidably coupled to the light source 111 and disposed adjacent to the socket 132. The threaded stem portion of the heat-sink 133 is threadedly coupled in the threaded bore of the socket 132. The optical fiber 112 is optically coupled to the light source 111. The electronic iris 160 is disposed adjacent to the bore of the threaded stem portion of the heat sink 133 and in the bore of the disc-shaped portion of the heat sink 133. The electronic iris 160 is axially aligned with the optical fiber 111. The electronic iris 160 is controlled by feedback from the CCD from the exposure control circuit. The exposure control circuit includes a control amount converting table which stores data on a gain control amount associated with data on a detected quantity of incident light and provides feedback to the electronic iris 160. On the basis of an output from the control amount converting table and light quantity gains of a light quantity variable mechanism the exposure control circuit adjusts the electronic iris 160.

An automatic iris control system which U.S. Pat. No. 4,300,167 teaches is electrically adjustable. The automatic iris control system is connected between a video camera and an optical input device which produces an optical image from a light directed upon and reflected from a subject. The optical image is directed onto the surface of an electronic imaging tube in the video camera and the optical image has a wide variation of reflected light due to variations in distance of the subject from the light source. The automatic iris control system has a mechanical iris and an iris drive motor which is located between the surface of the electronic imaging tube and the optical input device and which dynamically varies the intensity of the optical image applied to the electronic imaging tube of the video camera. A light intensity programming circuit establishes a desired light intensity level on the surface of the electronic imaging tube of the video camera. An automatic iris control circuit has a low gain amplifier, a weighted peak response detector, a comparator, a circuit which control current to the iris drive motor and a circuit which provides a feedback signal. The feedback signal represents the direction in which the iris drive motor must adjust the mechanical iris in order to control the light intensity on the surface of the electronic imaging tube of the video camera.

From the foregoing it can be seen that a combination electronic iris source and connector for use with a light source has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:

1. A combination electronic iris and optical connector for use with a light source, an optical fiber and a CCD which is optically coupled to the optical fiber and electrically coupled, said combination electronic iris and optical connector comprising:
   a. a socket having a threaded bore and being mechanically coupled to the light source;
   b. a plug adapted to be coupled to said socket, said plug having a bore for receiving the optical fiber;
   c. a heat sink having a disc-shaped portion having a bore for receiving the optical fiber and a threaded stem portion having a bore for receiving said optical fiber, said disc-shaped portion of said heat sink being slidably coupled to the light source and disposed adjacent to said socket and said threaded stem portion of said heat-sink being threadedly coupled in said threaded bore of said socket whereby the optical fiber is optically coupled to the light source; and
   d. an electronic iris disposed within the light source and axially aligned with said optical fiber whereby said electronic iris is controlled by feedback from the CCD.

2. A combination electronic iris and optical connector according to claim 1 wherein the CCD includes:
   a. a substrate with a plurality of charge coupled devices, said substrate being optically coupled to the optical fiber; and
   b. a detector optically coupled to said charge coupled devices and electrically coupled to said electronic iris whereby said detector detects light intensity on said substrate and then either opens or closes said electronic iris in a relative response thereto thereby controlling said light intensity on said substrate.

* * * * *